United States Patent [19]

Marchetti et al.

[11] 4,308,166
[45] Dec. 29, 1981

[54] PROCESS FOR THE EXTEMPORANEOUS PREPARATION OF LIPOSOMES

[75] Inventors: Enzo Marchetti; Umberto Bucciarelli, both of Rome, Italy

[73] Assignee: Istituto Farmacologico Serono S.p.A., Italy

[21] Appl. No.: 89,386

[22] Filed: Oct. 30, 1979

[30] Foreign Application Priority Data

Nov. 17, 1978 [IT] Italy ................ 51947 A/78

[51] Int. Cl.³ .............. B01J 13/02; A61K 9/50; A61K 9/64; A61K 37/40
[52] U.S. Cl. ...................... 252/316; 424/36; 424/179
[58] Field of Search ............ 252/316; 424/36, 179

[56] References Cited

U.S. PATENT DOCUMENTS

| | | | |
|---|---|---|---|
| 3,009,856 | 11/1961 | Bunce | 424/179 |
| 3,932,657 | 1/1976 | Rahman | 424/319 |
| 3,993,754 | 11/1976 | Rahman et al. | 424/177 |
| 4,224,179 | 9/1980 | Schneider | 252/316 |

Primary Examiner—Richard D. Lovering
Attorney, Agent, or Firm—Ostrolenk, Faber, Gerb & Soffen

[57] ABSTRACT

The extemperaneous preparation of liposomes incorporating englobed therapeutically active substances is effected by introducing an aspirated phopholipid emulsion into a container containing the active substance as a dry powder or lyophilate.

5 Claims, No Drawings

PROCESS FOR THE EXTEMPORANEOUS PREPARATION OF LIPOSOMES

As is known, liposomes are artificial sperules of phospholipids composed of a series of concentric layers alternated with aqueous compartments. Substances of various kinds may be "entrapped" within the aqueous compartments or the concentric layers.

Liposomes, prepared for the first time by Bangham (J Mol Biol 13(1), 238–59, 1965) and later so named by Sessa and Weissmann (J Lipid Res 1968, 9(3), 310–18) were first used as artificial models to study the properties of biologic membranes. It was, in fact, quickly recognized that the phospholipid walls of liposomes have properties perfectly analogous to those of erythrocytes, lisosomes and mitochondria as compared with various kinds of substances such as steroids, toxins, antibiotics, and drugs in general.

The practical potential of liposomes lies in the fact that these have been recognized as capable not only of englobing the most varied substances but also of protecting them from degradation processes and of orienting them toward specific target organs.

Unfortunately, the complexity of the processes for preparing liposomes containing therapeutically active substances has not yet permitted establishing a commercially effective production method. Moreover, there are serious stability problems with the compounds that it has been possible to prepare.

These and other problems, for example, the high cost of the preparations, pointed up the need for a simple and low-cost process for the preparation of liposomes containing active substances. By using the method of the present invention, one obtains liposomes containing therapeutically active substances through simple dissolution, at the moment of use, of the active substance with a phospholipid emulsion in water or physiologic solution, or buffer solution, followed by agitation. The preferred method consists in using the technique normally adopted for dissolving a dry powder or lyophilate with a solvent, that is:

- aspirate the phospholipid emulsion with a syringe;
- discharge the contents of the syringe into a container (vial or bottle) of the therapeutically active substance, in the dry or lyophilized state;
- agitate the vial or bottle to improve the solubility;
- aspirate the solution with the syringe, eventually discharging it again into the container to aspirate it anew.

At this point, the syringe contains a fine suspension of liposomes in an aqueous environment which englobe within their structure the therapeutically active substance.

As a phospholipid emulsion, any aqueous emulsion of phopholipids from soy beans, cerebral cortex, egg, etc., may be used.

A preferred emulsion is that prepared, starting with the yolk of a fresh egg, according to the method of Italian Pat. No. 989,501, of the same Applicant, entitled: "Single method for the extraction of phospholipids, lipids and phosvitin from the yolk of a hen's egg."

The following examples illustrate the invention without attributing limitations of any kind to them.

EXAMPLE 1

An ex-ovo phospholipid emulsion has been prepared according to the above-cited Italian Pat. No. 989,501, working in the following manner: 1000 fresh eggs are broken and the yolks are separated from the albumin. The yolks are split and poured into an extractor containing 70 liters of ethyl alcohol 90.5° at room temperature (22°–25° C.). After 24 hours of infusion, during which the coagulated mass is stirred frequently to facilitate extraction of the lipids, the alcoholic extract is filtered first through a layer of gauze placed in the base of the extractor and then across pleated filter paper. The filtrate, joined with a second alcoholic extract obtained by placing in infusion for 4 hours the residue of the first extraction with 50 liters of ethyl alcohol, is placed into double-walled still, with hot water circulating in the interspace, and the distillation of the alcohol is started under vacuum (20–30 mmHg). The distillation operation is continued until an approximately 25% alcohol content is reached; at this point 12.5 liters of sterile physiologic solution are poured into the still and the distillation is continued until the alcohol is completely eliminated.

The product remaining in the still is distributed into 11 sterile 5-liter flasks, each containing 2.5 liters of sterile physiologic solution; these are left to stand for about 12 hours to allow deposition of the phospholipids. At the end of this period, the supernatant physiologic solution is decanted; the sedimented product constitutes a stable emulsion which, suitably diluted, may be introduced directly into vials.

Analysis, effected by thin layer chromatography, of the emulsion's dispersed phase reveals the following percentage composition:

| | |
|---|---|
| Phosphatidylcholine (lecithin) | 71.4 |
| Phosphatidylethanolamine (cephalin) | 15.4 |
| Lysophosphatidylcholine | 7.3 |
| Sphyngomyelin | 4.1 |
| Phosphatidic acid | 0.4 |
| Other, non-identified phospholipids | 1.4 |
| | 100.0 |

Using the phospholipid emulsion prepared as described above, there were obtained five different suspensions employing the following techniques:

(1) Sonication. The phospholipid mixture is suspended in water ($\sim$50 mg/ml) and subjected to ultrasound treatment with an Ultratip apparatus (wave energy system) with a potency varying between 40 and 60 watts. The temperature is maintained between 4° and 6° C. for the entire duration of the process. After several minutes of sonication, there is obtained a suspension of transparent liposomes (SUV), of clear yellow color, which is eluted on a Sephadex G 50 column to separate the eventual micelles of greater dimensions.

(2) Vortex agitation. The phospholipid mixture in water is subjected to vortex stirring for one hour and is used without any further treatment.

(3) Manual agitation. The phospholipid mixture in water is used after having been subjected to manual stirring for 5 minutes.

(4) Syringe agitation. The phospholipid mixture in water is used after successive aspirations and expulsions in a syringe for intramuscular injections.

(5) The same technique described in (4) but with expulsion and aspiration of the liquid into a vial containing lyophilized adrenocortical extract having the following percentage composition:

| | |
|---|---|
| Aldosterone | 5.5% |
| Corticosterone | 26.4% |
| Cortisone | 13.7% |
| Hydrocortisone | 17.0% |
| 11-dehydrocorticosterone | 17.6% |
| 17-hydroxy-11-desoxycorticosterone | 5.1% |
| Others | 14.7% |

The five different suspensions were studied using infra-red (IR), ultra-violet (UV), nuclear magnetic resonance (NMR) and electron microscopy under the following experimental conditions:

(a) IR and UV Measurements

The infrared spectrum of the phospholipid mixture, alone and in the presence of the adrenocortical extract, was recorded with a Perkin-Elmer 577 spectrophotometer having a scan time of 15 minutes.

The corresponding ultraviolet spectra (solvent: petroleum ether 30–50) were recorded with a Beckman DK-2 spectrophotometer, using a quartz cell with a 1 cm edge.

(b) NMR Measurements

The $^{13}C$ spectra (in $D_2O$ and in $CDCl_3$) were recorded with a Bruker WH 90 spectrometer which operates at 22.63 MHz in a Fourier arrangement.

The experimental conditions are: impulse width 30°, number of impulses between 20000 and 30000, 16K of memory, SW of 6000 Hz, ambient temperature, internal lock on the solvent's deuterium ($CDCl_3$ or $D_2O$). The chemical shift values were determined in comparison with Tetramethylsilane (TMS) being used as an internal reference for the solutions in $CDCl_3$ and externally for the suspensions in $D_2O$. The proton spectra were recorded at 90 MHz with a Bruker HX90 instrument which operates on a continuous wave; DSS was used as the internal reference and lock. The samples were prepared using techniques 4 and 5 above described.

(c) Electronmicroscopy Measurements

The electron microphotographs were obtained using a Siemens Elmiskop 102 instrument and observations were made under negative contrast with phosphotungstic acid 2%.

RESULTS

IR and UV:

The IR spectrum of the phospholipid mixture permitting assignations of the signals present in it is shown in Table I.

From the UV spectrum, one can only deduce the presence of fatty acids with double bonds linked to the side chains of the esterified or free glycerol. The addition of the corticosteroid extract caused no appreciable change of the signals present in the spectra.

Electronmicroscopy:

The microphotographs show the results obtained with the following samples:
(1) manual agitation for 5 minutes.
 apparent diameter of the vesicles > 5000 Å
(2) vortex agitation for 1 hour
 apparent diameter of the vesicles 1000–10000 Å
(3) sonification for 15 minutes
 apparent diameter of the vesicles 300–1000 Å
(4) syringe agitation
 apparent diameter of the vesicles 1000–2500 Å
(5) syringe agitation (illustrations refer to the phospholipid mixture in the presence of the corticosteroid extract)
 apparent diameter of the vesicles 1000–2000 Å

On examining the microphotographs, it is seen that the method of preparing the phospholipid suspensions determines the structure of the vesicles formed. In fact, suspensions obtained by simple more or less prolonged agitation reveal vesicles that are generally larger, non-uniform in diameter, and structurally similar to the MLV type. Instead, suspensions obtained by use of the syringe reveal vesicles that are clearly smaller in dimensions than the preceding, much more homogeneous in diameter, and of the same type as those that can be prepared by using the sonication procedure (SUV).

NMR:

The proton NMR and the $^{13}C$ spectra of the phospholipid mixture in $CDCl_3$ furnish the chemical shift values (referred to TMS) of the diverse resonance bands reported in Tables II and III, together with some assignations.

The $^1H$ and $^{13}C$ spectra of the same mixture in $D_2O$ furnish the chemical shift values and the assignations reported in Tables IV and V respectively.

Generally, these spectra show much greater line widths as compared with corresponding spectra in $CDCl_3$ solutions.

In the $^{13}C$ spectrum, however, there are clearly noted several lines centered at 19.6, 60.26, and 63.58 ppm, much narrower and comparable in width to the spectra in chloroform.

The $^{13}C$ spectrum of the phospholipid mixture in the presence of adrenocortical extract in $D_2O$ and in $CDCl_3$ is substantially identical with that obtained in the absence of lyophilized extract.

EXAMPLE 2

To determine the degree to which an adrenocortical extract is englobed within a phospholipid emulsion used to form liposomes in the present invention, the following experiment was performed, using lyophilized vials each containing 390 micrograms of corticoid, of the following percentage composition (calculated as hydrocortisone):

| | |
|---|---|
| Tetrahydrocortisone | 0.20% |
| Aldosterone | 5.28% |
| 11-dehydrocorticosterone | 17.58% |
| Corticosterone | 26.38% |
| Cortisone | 13.78% |
| Hydrocortisone | 17.00% |
| 17-hydroxy-11-desoxycorticosterone | 5.13% |
| Other fractions | 14.65% |
| | 100.00% |

To release the adrenocortical extract in the phospholipid emulsion, the technique described at step 5 of Example 1 was adopted.

The experiments were conducted according to the following plan:
(1) A lyophilized vial containing 390 μg of adrenocortical extract was dissolved in 15 ml of $H_2O$ (Control), kept for 16 hours at 10° C. and then analyzed at the same time as the other solutions.
(2) Four lyophilized vials containing the same amount of adrenocortical extract were dissolved in 20 ml of phospholipid emulsion ex-ovo 5% in physiologic solution.

(2a) 10 ml of the corticosteroid solution in phospholipid emulsion were allowed to settle at circa 10° C. for 16 hours. Almost all the phospholipids remain at the bottom of the container; the supernatant liquid was clarified by centrifugation at 1000 rpm for 5 minutes. Five ml of the centrifuged liquid were diluted to 15 ml with $H_2O$.

(2b) 5 ml of solution 2), i.e., containing corticosteroids and phospholipids, not separated either by resting or centrifugation, were diluted to 15 ml with $H_2O$.

(3) At the same time as the 20 ml of phospholipid emulsion without corticosteroids, there were prepared two solutions with the same procedure used for solutions 2a and 2b, obtaining two solutions; 3a, used as a control for the analysis of solution 2a; and 3b, used as a control for solution 2b.

Analyses of all the solutions were performed by extracting 15 ml of each with 10 ml×4 chloroform. The chloroformed extracts were dehydrated with anhydrous sodium sulfate and vacuum dried. The residue, collected with 10 ml of 95° ethanol, was subjected (on 1 ml of alcoholic solution) to colorimetric reaction with tetrazolium blue. The following results were obtained:

CORTICOSTEROID DETERMINATIONS (μg/15 ml)

| Solution 1 Corticosteroids | Solution 2 Phospholipids + Corticosteriods | | Solution 3 Phospholipids Alone | |
|---|---|---|---|---|
| | 2a supernatant | 2b total | 3a supernatant | 3b total |
| 345 | 57 | 410 | 0 | 141 |

From the calculation $$\frac{345 - 57}{345} \times 100 = 83.5\%$$

one deduces that this is the percentage of corticosteroids retained by the phospholipids.

As a control, the calculation $$\frac{(410 - 141) - 57}{410 - 141} \times 100$$

furnishes the value of 79%, in good agreement with the preceding. (It should be noted that the phospholipids alone also give a reaction with the tetrazolium blue; this should be kept in mind.)

From the experiments above described, it is deduced that the phospholipids, in the form of liposomes, retain the greatest part (circa 80%) of the corticosteroids present in the solution.

EXAMPLE 3

Using the suspension of corticosteroids-containing liposomes prepared according to the present invention, there was performed a pharmacologic test of survival of adrenalectomized mice, working in the following manner.

The experiments were conducted on Morini strain Swiss mice transabdominally adrenalectomized under ether anesthesia. The mice were adrenalectomized immediately after weaning (median weight 10±1 g).

The adrenalectomized mice were divided into four groups: one group served as a control, the other three received a single injection of the lyophilized adrenal steroid mixture of the following composition: 11-desoxy-17-hydroxycorticosterone 6%; 11-dehydrocorticosterone 11.5%; hydrocortisone 31%; aldosterone 2.9%; corticosterone 18.22%; other fractions 4.6%. The mixture was dispersed in, respectively: distilled water, sesame oil; or in the phospholipid mixture obtained from the 5% egg yolk emulsion in physiologic solution used in Example 1, using the technique described at step 5 of the same Example.

The injection was made under the dorsal skin, in the interscapular area, 5, minutes before adrenalectomy; the total volumes injected were 0.4 ml per animal. The animals were maintained at a temperature of 22° C.±1°; relative humidity 60 with a 24-hour night and day rhythm (12 hours of light/24) for the entire duration of the experiment.

The mortality per hour, in both the treated and control groups, was recorded for 66 hours. The data were elaborated for differences, according to the Student "t" and Dunnet "t", for globality of the experimented, with the factorial method of R. A. Fisher, for the "comparison of ratios", during various hours of observation.

RESULTS

Analysis of the comparison of ratios, also carried out with the Fisher method applied to all the time intervals of our observations, revealed, as expected, a statistically significant difference in the survival of animals treated with the adrenal hormone mixture as compared to the untreated controls (Tables VI and VII). In the case of the aqueous vehicle, however, survival was limited to the 18th hour. Beyond this limit, there is practically no protection on the part of a dose of corticoids used when it is vehicled in water.

Conversely, the ratio of mice that survive with adrenocortical hormones vehicled in phospholipids as compared with controls is very evident (Table VI) and is already, from the twelfth hour, highly significant (Table VII). In the case of the animals treated with hormones vehicled in oil, the ratio of survival as compared to controls is statistically significant (P<0.05) starting with the 18th and ending with the 30th hour.

The survival percentage in relation to the vehicle shows, therefore, a clear-cut increase in hormonal protection on the part of the phospholipid vehicle (Table VI). In fact, compared with the animals treated with adrenocortical hormones in water, survival exceeds the 36th hour and is evident until almost the 66th hour (Table VII). Even the injection of adrenal hormones in oil appears clearly to prolong survival as compared to hormones in water; the protection afforded, however, is proportionately less than that obtained with adrenal hormones and phospholipid mixture. One-hundred percent of the animals treated with cortical hormones in an aqueous vehicle had expired by the thirtieth hour. By the sixtieth hour, 100% of the animals treated with cortical hormones in the oily vehicle had expired, while 25% of the animals in which the cortical hormones had been injected with the phospholipids still survived.

TABLE I

| Egg phospholipid suspension - IR Spectrum | |
|---|---|
| wave number (cm.$^{-1}$) | Assignations |
| 2915 and 2845 with shoulder at 2948 | stretching of $CH_2$ groups and $CH_3$ terminals |
| 1725 | stretching of CC ester group |

TABLE I-continued

Egg phospholipid suspension - IR Spectrum

| wave number (cm.$^{-1}$) | Assignments |
|---|---|
| 1460 and 1380 | bending of $CH_2$ groups and $CH_3$ terminals |
| 1235 | (a) wagging of $CH_2$ and $CH_3$ groups |
| | (b) stretching of PO group |
| 1090 and 1050 | (a) rocking of $CH_3$ group terminals |
| | (b) stretching of P—O—C group (aliphatic) |
| 970 | (a) deformities out of the plane of the group —CH=CH— (trans) of the sphyngomyelins |
| | (b) stretching of the P—O—C group (aliphatic) |

TABLE II

NMR Data - $^1H$ in $CDCl_3$

| δ (ppm of TMS) | | Assignments |
|---|---|---|
| 0.89 | | $CH_3$ terminals |
| 1.27 | | —$(CH_2)_n$—fat chains |
| 2.03 | | $CH_2$ allyl |
| 2.30 | | $CH_2CO$ |
| 2.83 | | =$CHCH_2CH$= |
| 3.37 | | $^+N(CH_3)_3$ |
| 3.91 | wide | $CH_2N$ full, $CH_2OP$ |
| 4.33 | multiplets | —$CH_2O$ glycerol |
| 5.36 | | CH=; $\overset{|}{\underset{|}{CH}}$—O |

TABLE III

NMR Data - $^{13}C$ in $CDCl_3$

| δ (ppm of TMS) | Assignments |
|---|---|
| 11.66 | —$CH_3$ |
| 13.89 | —$CH_3$ termimals |
| 18.52 | |
| 19.23 | |
| 20.95 | |
| 22.37 | $CH_2CH_3$ |
| 22.50 | |
| 23.70 | |
| 24.73 | —$CH_2CH_2CO$ |
| 25.44 | =$CHCH_2CH$= |
| 26.35 | |
| 27.03 | =$CH_2CH$= |
| 27.81 | |
| 28.07 | |
| 29.04 | |
| 29.13 | —$(CH_2)_n$—fat chains |
| 29.52 | |
| 31.34 | |
| 31.72 | $CH_2CH_2CH_3$ |
| 33.96 | |
| 34.12 | $CH_2CO$ |
| 35.61 | |
| 36.03 | |
| 36.35 | |
| 37.19 | |
| 39.36 | $CH_2N$ ethanolamine |
| 39.65 | |
| 42.18 | |
| 50.06 | |
| 54.15 | $^+N(CH_3)_3$ |
| 56.64 | carbons of the glycerol and alcohol chains which esterify the phosphate |
| 59.46 | |
| 62.91 | |
| 63.54 | |
| 66.16 | |
| 70.53 | $\overset{|}{\underset{|}{CH}}$—O |

TABLE III-continued

NMR Data - $^{13}C$ in $CDCl_3$

| δ (ppm of TMS) | Assignments |
|---|---|
| 71.11 | |
| 121.18 | $CH_2$ = (vinyls) |
| 127.75 | |
| 127.95 | |
| 128.17 | |
| 128.46 | CH=CH |
| 128.79 | |
| 128.88 | |
| 129.5 | |
| 129.82 | |
| 130.05 | |
| 130.31 | |
| 140.99 | $>C$ = (quaternary on double bond) |
| 172.93 | —CO ester |
| 173.32 | |

There is no variation in the position of the signals in the presence of the adrenocortical extract.

TABLE IV

NMR Data - $^1H$ in $D_2O$

| δ (ppm of DSS) | Assignments |
|---|---|
| 0.93 | $CH_3$ terminals |
| 1.33 | —$(CH_2)_n$—chain |
| 2.11 | $CH_2$ allyls, $CH_2CO$ |
| 3.29 | $^+N(CH_3)_3$ |

We are dealing with very wide bands; the signal of the CH= is hidden by that of the water (4.79 ppm).

TABLE V

NMR Data - $^{13}C$ in $D_2O$

| δ (ppm of TMS) | | Assignments |
|---|---|---|
| 16.6 | wide | —$CH_3$ terminals |
| 19.61* | | |
| 25.34 | wide | $CH_2CH_3$ |
| 31.72  35.44 | very wide | —$(CH_2)_n$—fat chains |
| 56.35 | wide band | $^+N(CH_3)_3$ |
| 56.93 | | |
| 60.26* | | |
| 65.38* | | |
| 130.62 | very wide | CH= |
| 131.07 | | |

*these signals are narrow with Δr ½ comparable to that of the signals in the chloroform solution.

In the presence of adrenocortical extract, the $^{13}C$ spectrum is identical, except for three narrow and well-defined signals at 66.06, 72.21 and 73.79 ppm.

TABLE VI

HOURS OF SURVIVAL OF MICE ADRENALECTOMIZED AND TREATED WITH ADRENOCORTICAL EXTRACT IN AQUEOUS, OILY, PHOSPHOLIPID VEHICLE

| TREATMENT | Hours of survival $\bar{x}$ ± SE | Dunnet "t" | Significance |
|---|---|---|---|
| (1) Distilled water (Controls) | 14 ± 4.671 | 1 vs 2  0.8 | N.S. |
| (2) Adrenocortical extract in distilled water | 18 ± 7.441 | 1 vs 3  2.3 | 0.05 |
| (3) Adrenocortical extract in sesame oil | 29 ± 16.405 | 1 vs 4  4.9 | 0.01 |
| | | 2 vs 4  4.0 | 0.01 |
| (4) Adrenocortical extract in phospholipids | 40 ± 20.674 | 2 vs 3  1.4 | N.S. |

TABLE VII

COMPARISON BETWEEN A CONTROL AND THREE TREATMENTS STUDIED BETWEEN THE SIXTH AND SIXTY-SIXTH HOUR CARRIED OUT ACCORDING TO THE "DIRECT OR FACTORIAL METHOD" OF R.A. FISHER

| | % PROBABILITY | | | | | | | | | |
|---|---|---|---|---|---|---|---|---|---|---|
| | 6 h | 12 h | 18 h | 24 h | 30 h | 36 h | 48 h | 54 h | 60 h | 66 h |
| Controls vs ECS + $H_2O$ | 50 | 23.3 | 4.7* | 23.9 | 100.0 | 100.0 | 100.0 | 100.0 | 100.0 | 100.0 |
| Controls vs ECS + phospholipid | 23.9 | 3.2* | 0.1** | 0.2** | 0.7** | 0.7** | 10.9 | 10.9 | 10.9 | 50.0 |
| Controls vs ECS + oil | 38.6 | 12.8 | 0.9** | 3.6* | 3.6* | 36.8 | 36.8 | 36.8 | 100.0 | 100.0 |
| ECS + $H_2O$ vs ECS + phospholipid | 50.0 | 14.0 | 1.7** | 4.0* | 0.7** | 0.7** | 10.9 | 10.9 | 10.9 | 50.0 |
| ECS + $H_2O$ vs ECS + oil | 63.2 | 29.8 | 22.9 | 19.9 | 3.6* | 36.8 | 36.8 | 36.8 | 100.0 | 100.0 |
| ECS + phospholipid vs ECS + oil | 100.0 | 49.1 | 19.9 | 30.0 | 35.0 | 12.8 | 39.7 | 39.7 | 36.8 | 63.2 |

*significant to the 5% certainty limit
**significant to the 1% certainty limit
ECS = estratto corticosurrenale, i.e., adrenocortical extract.)

We claim:

1. A process for the extemporaneous preparation of liposomes incorporating englobulated therapeutically active substances characterized in that an aspirated phospholipid emulsion in water or physiologic solution is introduced into a container containing the active substance as a dry powder or lyophilate.

2. A process according to claim 1 characterized in that as a phospholipid emulsion there is used a phospholipid emulsion prepared from the yolk of a hen's egg.

3. A process according to claim 1 for the preparation of liposomes incorporating therapeutically active substances characterized in that the active substance is an adrenocortical extract.

4. A process according to claim 1 characterized in that the emulsion, after introduction to the container, is agitated, aspirated and introduced into a container.

5. A process according to claim 4 characterized in that the aspiration and introduction steps are effected with a syringe.

* * * * *